United States Patent [19]

Hall et al.

[11] 4,405,798

[45] Sep. 20, 1983

[54] ACRYLATE AND METHACRYLATE MONOESTERS OF PENTAERYTHRITOL AND PENTAERYTHRITOL ORTHOESTERS AND POLYMERS AND COPOLYMERS DERIVED THEREFROM

[75] Inventors: Henry K. Hall, Tucson, Ariz.; Donald R. Wilson, Warren, N.J.

[73] Assignee: Celanese Corporation, New York, N.Y.

[21] Appl. No.: 248,183

[22] Filed: Mar. 30, 1981

[51] Int. Cl.³ .......................................... C07D 319/14
[52] U.S. Cl. ................................ 549/363; 260/29.6 R
[58] Field of Search ................... 260/340.7; 560/224; 549/363

[56] References Cited

U.S. PATENT DOCUMENTS

| | | | |
|---|---|---|---|
| 3,184,441 | 5/1965 | Fang | 260/340.9 R |
| 3,577,438 | 5/1971 | Melaas | 549/363 |
| 3,686,224 | 8/1972 | Deffner | 549/363 |
| 4,187,383 | 2/1980 | Cowherd et al. | 560/224 |

FOREIGN PATENT DOCUMENTS

| | | | |
|---|---|---|---|
| 56-6108792 | 8/1981 | Japan | 549/363 |
| 56-6108793 | 8/1981 | Japan | 549/363 |

*Primary Examiner*—Ethel G. Love
*Attorney, Agent, or Firm*—Scully, Scott, Murphy & Presser

[57] ABSTRACT

Acrylate and methacrylate monoesters of pentaerythritol and pentaerythritol orthoesters are provided. These orthoesters are especially useful as monomers for the preparation of polymers and copolymers having a variety of industrial applications.

3 Claims, No Drawings

ACRYLATE AND METHACRYLATE MONOESTERS OF PENTAERYTHRITOL AND PENTAERYTHRITOL ORTHOESTERS AND POLYMERS AND COPOLYMERS DERIVED THEREFROM

BACKGROUND OF THE INVENTION

1. Field of the Invention

The present invention relates to monoesters derived from ethylenically unsaturated carboxylic acids and polyhydroxy alcohols and to polymers and copolymers prepared from such monoesters.

2. Description of the Prior Art

Multifunctional polyol derivatives of acrylic or methacrylic acid esters of polyols in which at least two hydroxyl groups are esterified and synthetic resins prepared from such derivatives are known. U.S. Pat. No. 3,943,103 describes a polyfunctional reactive solvent which confers crosslink density to a radiation curable resin composition containing a low molecular weight vinyl acetate polymer and a monofunctional acrylate ester. The polyfunctional reactive solvent is polyacrylate ester having from 2 to 6 acrylyl groups such as pentaerythritol di-, tri-, or tetra-acrylate. The monofunctional ester is derived from acrylic or methacrylic acid and a monohydroxyl compound, e.g., methyl methacrylate, butyl acrylate, isobutyl acrylate, 2-ethylhexyl acrylate, 2-hydroxyethyl acrylate, dicyclopentenyl acrylate, (methylcarbamyl)ethyl acrylate, 2-phenoxyethyl acrylate, 2-methoxyethyl acrylate, 2-(N,N-diethylamino)-ethyl acrylate and oleic or ricinoleic acid acrylate. U.S. Pat. No. 4,145,319 describes a water-reducible alkyd resin derived in part from an ester of an alpha, beta-ethylenically unsaturated carboxylic acid of a polyesterified polyol containing at least two hydroxy groups, e.g., an acrylic or methacrylic acid ester of pentaerythritol, dipentaerythritol or tripentaerythritol.

Since the acrylic and methacrylic acid esters of multifunctional polyols heretofore known are obtained from the direct esterification of the acid and polyol reactants, the resulting esters inevitably are mixtures of mono- and polyacrylic and methacrylic acid esters, up to the entire number of hydroxyl groups originally present in the starting polyol.

SUMMARY OF THE INVENTION

In accordance with the present invention, an alpha, beta-ethylenically unsaturated monoester is provided which can be represented by the general formula:

$$CH_2=C(R_1)-C(O)-OCH_2-R_2$$

in which group $R_1$ is hydrogen or a methyl group and $R_2$ is either the group

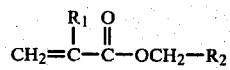

wherein $R_3$ is hydrogen or a non-functional organic group, preferably a lower alkyl group such as methyl or ethyl, or $R_2$ is the group

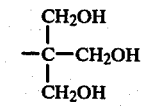

Monoesters of a pentaerythritol orthoester can be prepared by the esterification of acrylic acid, methacrylic acid or corresponding acyl halide thereof with a pentaerythritol orthoester as in the equation:

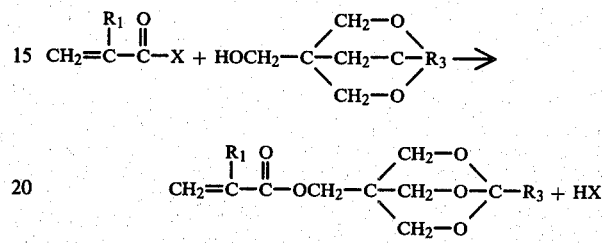

In the above, $R_1$ and $R_3$ have the same meanings given above and X is hydroxyl or halogen. When the acid halide is employed, it is generally preferred to include an acid receptor in the reaction medium to take up the coproduced haloacid.

Alternatively, the monoesters of pentaerythritol orthoester can be prepared by transesterifying the orthoester with an acrylic or methacrylic acid ester accompanied by the distillation of the co-produced hydroxyl compound as in the equation:

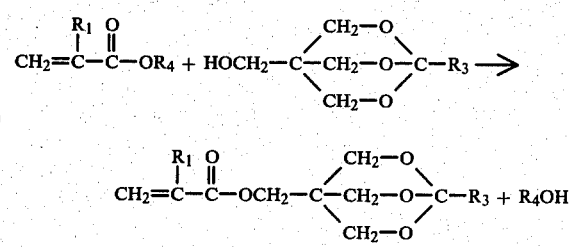

As a third alternative, the monoesters of pentaerythritol orthoester can be prepared by reacting a monobromo pentaerythritol orthoester with cuprous acrylate or cuprous methacrylate as in the equation:

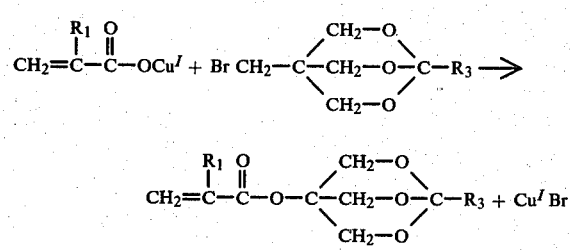

In the above, $R_1$ and $R_3$ have the same meanings given above and $R_4$ is a hydrocarbyl group, preferably a lower alkyl group such as methyl or ethyl.

Monoesters of pentaerythritol can be readily prepared by hydrolysis of the monoesters of pentaerythritol orthoester as in the equation:

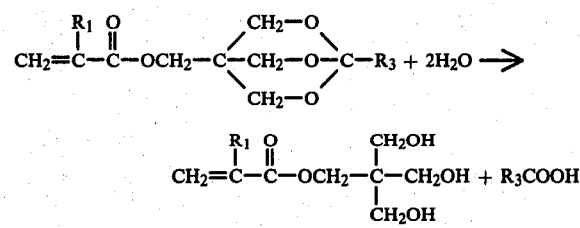

Unlike the multifunctional polyol derivatives known in the art and described above, the monoesters herein are capable of providing high molecular weight polymers due to their lack, or minimization, of chain transfer hydrogens. Accordingly, further in accordance with the present invention, the acrylate and methacrylate monoesters of pentaerythritol and pentaerythritol orthoesters can be homopolymerized or copolymerized with other ethylenically unsaturated monomers to provide relatively high molecular weight water soluble resins which are useful as thickeners, suspension agents, flocculants, and the like. The relatively low molecular weight resins impart advantageous wetting and adhesion properties to coating compositions formulated therewith and can be crosslinked, for example, with isocyanates and polyisocyanates, to provide industrially useful thermosetting coatings.

Another important use of the orthoesters herein is as latent crosslinkers for emulsion polymers and latices.

The conditions under which the various esterification, transesterification, hydrolysis and polymerization reactions referred to above are carried out are themselves well known and do not constitute a part of the invention herein per se.

DESCRIPTION OF THE PREFERRED EMBODIMENTS

The orthoester of pentaerythritol or monobromo pentaerythritol can be readily and conveniently obtained by reacting pentaerythritol or monobromo pentaerythritol with an orthoester of the formula $R_3C(OR_5)_3$ in which $R_3$ has the same meaning given above and $R_5$ is a lower alkyl group, preferably a methyl or ethyl group, in the presence of a proton donor such as a strong mineral or organic acid accompanied by distillation of the co-produced lower alkanol as in the equation:

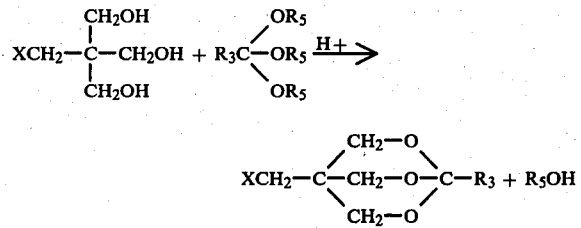

In the above equation, X represents a hydroxyl group or a halogen atom.

The pentaerythritol orthoester is esterified or interesterified as shown in the equations above to provide the acrylate and/or methacrylate monoester which can thereafter be hydrolyzed, if desired, to the corresponding pentaerythritol monoester.

The monoester can be polymerized alone or together with one or more ethylenically unsaturated monomers polymerizable therewith. The relative proportions of acrylic/methacrylic monoester to such other monomers with which the former can be copolymerized can vary widely. For some applications, the amount of interpolymerized comonomer should not be so high as to significantly reduce the water soluble properties of the resulting resins. Among the ethylenically unsaturated monomers which can be copolymerized with the monoesters of this invention are those of the general formula:

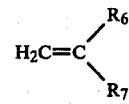

wherein $R_6$ and $R_7$ each are representative of such groups as hydrogen, lower acyclic, especially methyl, ethyl, propyl and vinyl, lower cycloaliphatic, especially cyclohexyl and cyclohexenyl, aryl, especially phenyl, carboxylic acid, acetate, alkoxy amide, acetamide, and the like. Ethylenically unsaturated monomers conforming to such formula are ethylene, propylene, butene-1, vinyl cyclohexane, vinyl cyclohexene, styrene, vinyl styrene, vinyl toluene, acrylic acid, methacrylic acid, vinyl formate, vinyl acetate, vinyl propionate, vinyl butyrate, crotonic acid, itaconic acid, vinyl fluoride, vinyl chloride, vinylidene fluoride, vinylidene chloride, tetrafluoroethylene, acrylamide, methacrylamide, methacrylonitrile, acrolein, methyl vinyl ether, ethyl vinyl ether, vinyl ketone, ethyl vinyl ketone, allyl acetate, allyl propionate, diethyl maleate, etc.

The monoesters herein, and if present, other monomers copolymerizable therewith, can be readily polymerized in a known manner employing any of the free radical polymerization catalysts heretofore used in the polymerization of ethylenic monomers, e.g., inorganic peroxides such as hydrogen peroxide, sodium perchlorate and sodium perborate, inorganic persulfates such as sodium persulfate, potassium persulfate and ammonium persulfate and reducing agents such as sodium bisulfite.

The homopolymers and copolymers of the present invention can be represented by the general formula:

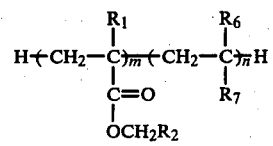

wherein $R_1$, $R_2$, $R_6$ and $R_7$ each have the same meanings given above and the sum of the interpolymerized units m is at least about 10, the sum of the interpolymerized units n is equal to zero or greater than 1, the sum of m+n is from about 10 to about 10,000 and preferably from about 100 to about 500 and the ratio of m to n is from about 100:1 to about 1:100 and preferably, from about 10 to 1 to about 1 to 10.

The following examples are further illustrative of the invention.

EXAMPLE 1

This example illustrates the preparation of the starting hydroxymethyl pentaerythritol orthoester.

In a large sublimation apparatus equipped with a side arm are mixed: 6.8 g (0.05 mole) pentaerythritol, 7.4 g (0.05 mole) triethyl orthoformate, 150 ml dioctyl phthalate (DOP) and a trace of anhydrous p-toluenesulfonic acid. Magnetic stirring is begun vigorously. The sublimator is immersed in an oilbath at 140° C. Ater 2.5 molequivalents of ethanol have been collected, the bath temperature is raised to 195° C., vacuum is applied to the apparatus (0.05 mm Hg) and the cold finger is cooled with a methanol-Dry Ice mixture to about −50° C. After about 15 minutes, crystals have collected on the cold finger, the DOP solution has cleared and some DOP has distilled. At this point, the reaction is stopped. The crystals are washed with hexane to remove DOP, and dissolved in chloroform leaving behind any polymer formed. An additional crop of crystals can be recovered from the distilled DOP in a similar manner. The alcohol is recrystallized from benzene, avoiding prolonged heating.

The resulting product can be represented by the structural formula:

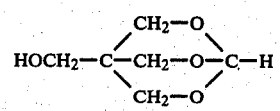

4-hydroxymethyl-2,6,7-trioxabicyclo[2.2.2]octane

Yield: 3.6 g (50%)

EXAMPLE 2

This example illustrates the preparation of acryloxy methyl orthoester of pentaerythritol by reaction of the hydroxy-methyl pentaerythritol orthoester prepared as in Example 1 with acryloyl chloride.

4-Hydroxymethyl-2,6,7-trioxabicyclo[2.2.2]octane (4.2 g, 30 mmole) is dissolved in 30 ml dry tetrahydrofuran in the presence of a trace of 3,5-di-t-butylcatechol and 30 ml (0.3 mmole) of dry triethyl amine at 0° C. Acryloyl chloride (2.7 g, 30 mmole) dissolved in 10 ml tetrahydrofuran is added slowly. The mixture is stirred for an additional hour. The precipitate is filtered off and the solvent is evaporated. The residue is dissolved in chloroform and the solution is run through a silicagel column to remove any possible residual quantity of triethylamine hydrochloride which causes polymerizations in attempts to recrystallize the acrylate. The obtained product (m.p. 86°–87° C.) is recrystallized from hexane and can be represented by the structural formula:

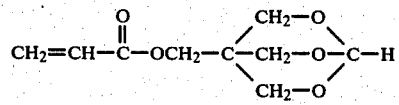

4-acryloxymethyl-2,6,7-trioxabicyclo[2.2.2]octane

Yield: 3.0 g (53%)

EXAMPLE 3

This example illustrates another procedure for preparing acryloxy methyl orthoester of pentaerythritol, i.e., the reaction of 4-bromomethyl-2,6,7-trioxabicyclo[2.2.2]octane with cuprous acrylate.

A. PREPARATION OF MONOBROMOPENTAERYTHRITOL

The synthesis of monobromopentaerythritol is described by S. Wawzonek, et al., *Org. Synth.* Vol. IV, 681 (1963) which is incorporated be reference herein. The synthesis described herein is improved over the procedure described by Wawzonek, et al. in adding acetic anhydride to the reaction mixture which increases the hydrobromic acid concentration from 48% to 66%. The product can then be purified by taking advantage of the difference in solubility of the starting material and the products formed.

In a 2 liter, three-necked flask equipped with a reflux condenser and an addition funnel are placed 200 g pentaerythritol (1.47 mole) and 16 ml 48% hydrobromic acid in about 500 ml glacial acetic acid. The mixture is refluxed for about one-half hour until all pentaerythritol is dissolved. Then, 170 ml 48% hydrobromic acid are added, followed by 310 ml acetic anhydride and the mixture is refluxed for 3 hours. Then, 94 ml 48% hydrobromic acid followed by 150 ml acetic anhydride are added and the mixture is refluxed for an additional 3 hours. The acetic acid is then removed as completely as possible on a rotary evaporator. Ethanol (95%, 750 ml) and 17 ml 48% hydrobromic acid are then added to the residue. The flask is equipped with 1 m Vigreux column and the azeotrope ethyl acetate/ethanol is slowly distilled off. When 500 ml distillate has been collected, an additional 750 ml 95% ethanol is added and the distillation is continued until about 400 ml is left over. After cooling, the precipitated pentaerythritol is filtered off. The solvent is evaporated and the residue is dissolved in water. The aqueous phase is extracted twice with carbon tetrachloride and twice with ether. The water is evaporated on the rotary evaporator and the last traces of water are removed by azeotropic distillation with toluene using a Dean-Stark trap. The solid is recrystallized from chloroform containing 10% acetonitrile. The first crop yielded 190 g monobromopentaerythritol. The total yield is 70%.

Monobromopentaerythritol (m.p. 72° C./lit. 76° C.) is very slightly soluble in chloroform, very soluble in ethanol, sec. butanol and acetonitrile, and insoluble in ether.

B. PREPARATION OF 4-BROMOMETHYL-2,6,7-TRIOXABICYCLO[2.2.2]OCTANE

Monobromopentaerythritol from A (10 g, 0.05 mole) and 9 ml triethylorthoformate (0.05 mole) are mixed in a sublimation apparatus equipped with a side arm. The mixture is heated to about 100° C. with magnetic stirring, and 1,5 equivalents of ethanol are allowed to distill out. Then about 100 ml dioctyl phthalate and a trace of anhydrous p-toluenesulfonic acid are added. Under vacuum the mixture is heated to about 140°–150° C. Periodically the collected crystals are removed from the cold finger. After about 3 hours no more compound sublimes. The yield of 4-bromoethyl-2,6,7-trioxabicyclo[2.2.2]octane is 6.5 g (60%).

C. PREPARATION OF CUPROUS ACRYLATE

Cupric acrylate (12 g, 0.058 mole) is mixed with about 250 ml dry acetonitrile, 30 g (0.5 mole) copper foil, 5 ml of acrylic acid, a few molecular sieves and a trace of radical inhibitor. The reaction mixture is stirred for 24 hours under nitrogen atmosphere until all the blue color disappears. Some white precipitate is formed. This precipitate and the solution are decanted from the remaining copper in a glovebag under nitrogen atmosphere and added to approximately 600 ml dry ether. The formed white precipitate is filtered off and dried, still under nitrogen. The yield of cuprous acrylate is 12.6 g (81%).

D. PREPARATION OF 4-ACRYLOXYMETHYL-2,6,7-TRIOXABICY-CLO[2.2.2]OCTANE

Cuprous acrylate from C. (0.017 g, 0.08 mole) and 4-bromomethyl-2,6,7-trioxabicyclo[2.2.2]octane from B. (12.5 g, 0.06 mole) are dissolved in 100 ml dry pyridine under nitrogen atmosphere. Some triethylamine radical inhibitor is added. The mixture is refluxed for 3 hours. The pyridine is completely evaporated. The green solids are ground up and placed in a soxhlet for extraction with hexane for 24 hours. The hexane is evaporated and the solids are dissolved in chloroform. The solution is passed through a short silicagel column to remove any remaining copper salts. The acrylate is recrystallized from hexane. Long white needles of 4-acryloxymethyl-2,6,7-trioxabicyclo[2.2.2]octane are recovered.

Yield: 6 g (60%)

EXAMPLE 4

This example illustrates the process of hydrolyzing 4-acryloxymethyl-2,6,7-trioxabicyclo[2.2.2]octane and the products resulting therefrom.

4-Acryloxymethyl-2,6,7-trioxabicyclo[2.2.2]octane (3 g) is mixed with 30 ml distilled water at room temperature. The mixture becomes homogeneous after ½ hour. The NMR spectrum indicates only partial hydrolysis has taken place, the partial hydrolyzate having the structure:

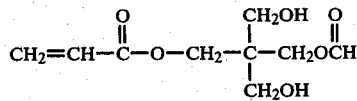

The reaction mixture is then heated to 70° C. The NMR spectrum of the reaction mixture is checked periodically to follow the reaction. After 4.5 hours the reaction is complete. The water and formed formic acid are evaporated and the reaction product is dried under vacuum. A glue-like material is obtained which does not crystallize after 3 days at −10° C. The material can be pulled into fibers several feet long. The product pentaerythritol monoacrylate which can be represented by the structure

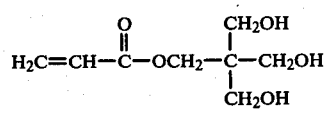

is insoluble in all common organic solvents including chloroform and acetonitrile.

EXAMPLE 5

The procedure of Example 2 is substantially repeated except that 4-hydroxymethyl-2,6,7-trioxabicyclo[2.2.2]octane is reacted with methacroyl chloride to provide the orthoester (m.p. 89°-91° C.):

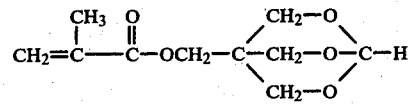

Yield: 45%

EXAMPLE 6

This example illustrates the partial and complete hydrolysis of the orthoester product of Example 5.

4-Methyacryloxymethyl-2,6,7-trioxabicyclo[2.2.2]octane (30 mg) is mixed with 1 ml of water. After 2 hours at 60° C. dissolution occurs and the NMR spectrum indicates partial hydrolysis to:

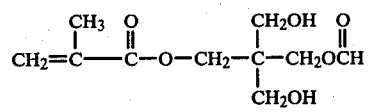

After 20 hours at 60° C., complete hydrolysis occurs to pentaerythritol monomethacrylate which can be represented by the structural formula

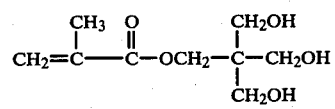

EXAMPLE 7

This example illustrates the preparation of 1-methyl-4-hydroxymethyl-2,6,7-trioxabicyclo[2.2.2]octane.

Pentaerythritol (13.6 g, 0.1 mole), triethyl orthoformate (16 g, 0.1 mole), a trace of p-toluenesulfonic acid and 100 ml dioctyl phthalate are mixed in a flask at 140° C. After the theoretical amount of ethanol has distilled out, the temperature is raised to 180°–190° C. and the pressure is reduced to <0.5 mm Hg. A white product crystallized in the condenser and is recrystallized from benzene. The product orthoester (m.p. 112° C.) can be represented by the structural formula

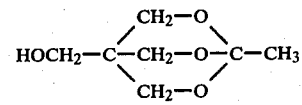

1-methyl-4-hydroxymethyl-2,6,7-trioxabicyclo[2.2.2]octane

Yield: 8.0 g (50%)

EXAMPLE 8

This example illustrates the conversion of the product orthoester of Example 7 to the corresponding methacryloxymethyl orthoester derivative.

Methacryloyl chloride (6.0 g, 0.06 mole) in 200 ml tetrahydrofuran is slowly added to a flask containing 9.0 g (0.06 mole), 60 ml triethylamine (0.6 mole) and a trace of radical inhibitor in 50 ml tetrahydrofuran at 0° C. The mixture is stirred for 1 hour, the precipitate is filtered off and the solvent is evaporated. The residue dissolved in chloroform is passed through a silicagel column and recrystallized from hexane. The product orthoester (m.p. 86° C.) can be represented by the structural formula

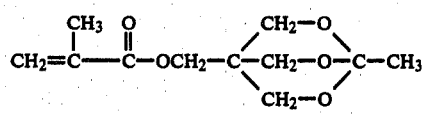

1-methyl-4-methacryloxymethyl-2,6,7-trioxabicyclo[2.2.2]octane

Yield: 5.4 g (40%)

EXAMPLE 9

This example illustrates the hydrolysis of the orthoester product of Example 8.

1-Methyl-4-methacryloxymethyl-2,6,7-trioxabicyclo[2.2.2]octane (50 mg) is mixed with 1 ml water. After 2 hours dissolution occurs and the resulting solution contains the partially hydrolyzed product of the structure

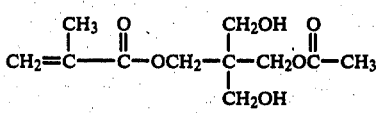

The foregoing product does not hydrolyze further to pentaerythritol monomethacrylate even at higher temperature. Addition of acid results in decomposition of the material.

EXAMPLE 10

This example illustrates the polymerization of 4-acryloxymethyl-2,6,7-trioxabicyclo[2.2.2]octane.

To a 1 g benzene solution of 4-acryloxymethyl-2,6,7-trioxabicyclo[2.2.2]octane is added 20 mg azobisisobutyronitrile (AIBN) initiator. The solution is purged with argon and heated at 80° C. for 6 hours. At this time, the solution is extremely viscous and cools to a brittle clear glass. The resulting polymer, poly(4-acryloxymethyl-2,6,7-trioxabicyclo[2.2.2]octane) which is represented by the structure

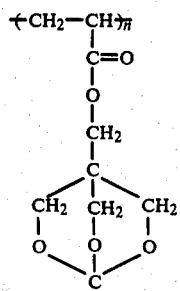

n = 100 to 500 has an inherent viscosity (0.1%, chloroform) of 0.53 dl.g.$^{-1}$

EXAMPLE 11

This example illustrates the hydrolysis of poly(4-acryloxymethyl-2,6,7-trioxabicyclo[2.2.2]octane) to poly(pentaerythritol monoacrylate).

Poly(4-acryloxymethyl-2,6,7-trioxabicyclo[2.2.2]octane) (50 mg) is mixed with 1 ml deuterated water in an NMR tube with 4 mole % formic acid. The heterogeneous mixture is heated to 70° C. for 3 hours until homogeneous. The NMR spectrum indicates only partial hydrolysis, to a polymer of the structure

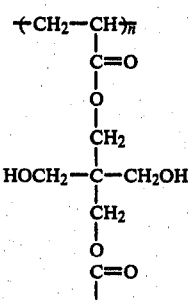

n = 100 to 500

After 2 weeks at room temperature the following NMR spectrum indicated that complete hydrolysis had taken place to poly(pentaerythritol monoacrylate)

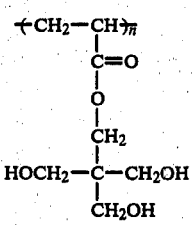

n = 100 to 500

EXAMPLE 12

This example illustrates the polymerization of 4-methacryloxymethyl-2,6,7-trioxabicyclo[2.2.2]octane.

The polymerization is carried out substantially in accordance with the procedure described in Example 10. The resulting polymer, poly(4-methacryloxymethyl-2,6,7-trioxabicyclo[2.2.2]octane), which can be represented by the formula

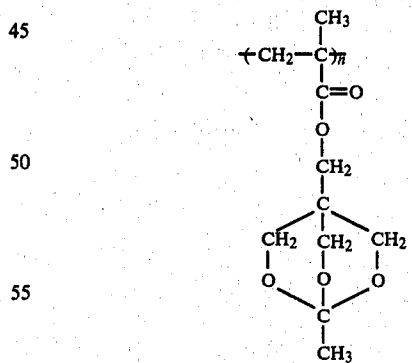

n = 100 to 500 is soluble in dimethyl sulfoxide.

EXAMPLE 13

The orthoester product of Example 8 is polymerized in much the same manner as described in Example 10. The resulting polymer, poly(1-methyl-4-methacryloxymethyl-2,6,7-trioxabicyclo[2.2.2]octane), which can be represented by the formula and sodium thiosulfate are chosen as initiating system, a Y-tube is used. The mixture is degassed twice and then the vials are sealed. The pentaerythritol monoacrylate is polymerized under the conditions described in Table I below. For the measurement of the inherent viscosity, the solutions are diluted to 10 ml. The polymers, which have a structure as shown in Example 11, are isolated by freeze-drying.

TABLE I
POLYMERIZATION OF PENTAERYTHRITOL MONOACRYLATE

| Amount of Pentaerythritol Monoacrylate | Initiator $K_2S_2O_8$ | $Na_2S_2O_3$ | Total Volume | Method$^a$ | $t^b$ (sec) | $n_{inh}{}^b$ | Remarks |
|---|---|---|---|---|---|---|---|
| 250 mg | 5 mg = 1,5 mole % | — | 4 ml | UV/45° | — | — | contains gel |
| 250 mg | 5 mg = 1,5 mole % | — | 4 ml | 80° | — | — | contains gel |
| 190 mg | 5 mg = 2 mole % | — | 10 ml | UV/45° | — | $c$ | viscous |
| 380 mg | 5 mg = 1 mole % | — | 10 ml | UV/45° | 140.8 | 0.25 | |
| 190 mg | 0.25 mg = 0.1 mole % | — | 2 ml | UV/45° | 241.9 | 0.79 | |
| 190 mg | 0.12 mg = 0.025 mole % | — | 2 ml | UV/45° | 157.8 | 0.57 | |
| 190 mg | 5 mg = 1 mole % | 5 mg = 2 mole % | 2 ml | 25° | 118.9 | 0.45 | |
| 190 mg | 0.5 mg = 0.1 mole % | 0.5 mg = 0.2 mole % | 2 ml | 25° | 134.7 | 0.49 | |
| 190 mg | 0.25 mg = 0.05 mole % | 0.25 mg = 0.1 mole % | 2 ml | 25° | 333.2 | 0.96 | |

$^a$All runs for 16 hours and with stirring except for first two, all runs went to 100%.
$^b$t = flow time in an Ostwald viscosimeter, solvent is water, $t_o$ = 53.6 sec., 30° C., solutions diluted to 10 ml.
$^c$Polymers were isolated and impossible to redissolve.

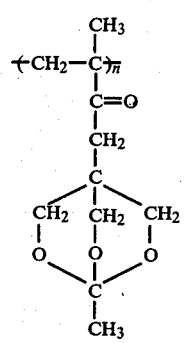

n = 100 to 500 is soluble in chloroform and acetone.

EXAMPLE 14

This example illustrates the polymerization of pentaerythritol monoacrylate (Example 4).

4-Acryloxymethyl-2,6,7-trioxabicyclo[2.2.2]octane, 1 g, is mixed with 10 ml redistilled water. The bicyclic orthoester is hydrolyzed to pentaerythritol monoacrylate at 60° C. for 4 hours. The only by-product formed is formic acid which does not interfere with the radical polymerization. The water solution is divided in several vials and initiator is added. When potassium persulfate

EXAMPLE 15

This example illustrates the polymerization of the partially hydrolyzed monomer produced substantially in accordance with the hydrolysis process described in Example 9.

Polymerization of this compound follows generally the same procedure described in Example 14. The resulting polymer, which conforms to the polymeric structure given in Example 11, precipitates out of the water as it is formed. After drying, the polymer is dissolved in hexafluoroisopropanol and precipitated in ether. A white powder is obtained.

EXAMPLES 16–30

The following examples, the conditions and results of which are set forth in Table II below, are further illustrative of homopolymerizations of the orthoester monomers of the present invention.

TABLE II
HOMOPOLYMERIZATION OF VARIOUS ORTHOESTER MONOMERS

| Example | Orthoester Monomer | Amount of Monomer | Conditions | Time | Initiator | Initiator Amount | Solvent | Yield % | $n_{inh}$ | Remarks |
|---|---|---|---|---|---|---|---|---|---|---|
| | $a$ | 200 mg 5 | UV/40° | 20 hrs | benzoyl peroxide | 1 mole % | benzene | 90 | — | not soluble (gel) |
| | $a$ | 200 mg 5 | UV/40° | 20 hrs | AIBN | 1 mole % | acetone | ? | — | not soluble (solid) |
| | $a$ | 200 mg 5 | UV/40° | 3 hrs | AIBN | 1 mole % | benzene | 0 | — | |
| | $a$ | 200 mg 5 | UV/40° | 8 hrs | AIBN | 1 mole % | benzene | 10 | — | |
| | $a$ | 250 mg 5 | UV/40° | 20 hrs | AIBN | 1 mole % | benzene | 90 | — | not soluble (gel) |
| | $a$ | 200 mg 5 | 80° | 20 hrs | AIBN | 1 mole % | benzene | 85 | — | not soluble |
| | $a$ | 202 mg 5 | UV/40° | 16 hrs | AIBN | 1 mole % | $(CF_3)_2CHOH$ | 100 | | |
| | $a$ | 200 mg 5 | UV/40° | 16 hrs | AIBN | 0.25 mole % | Sulfolane | 100 | | polymer does not completely redissolve after precipitation |

TABLE II-continued
HOMOPOLYMERIZATION OF VARIOUS ORTHOESTER MONOMERS

| Example | Orthoester Monomer | Amount of Monomer | Conditions | Time | Initiator | Initiator Amount | Solvent | Yield % | $n_{inh}$ | Remarks |
|---|---|---|---|---|---|---|---|---|---|---|
| | a | 200 mg 5 | UV/40° | 16 hrs | AIBN | 1 mole % | Sulfolane | 98 | $0.2^d$ | |
| | a | 200 mg 5 | UV/40° | 16 hrs | AIBN | 0.5 mole % | Sulfolane | 100 | $0.2^d$ | |
| | b | 50 mg 11 | UV/40° | 20 hrs | AIBN | 5 mole % | benzene | 30 | | not soluble |
| | b | 200 mg 11 | UV/40° | 20 hrs | AIBN | 5 mole % | sulfolane | 75 | $0.92^e$ | soluble |
| | c | 230 mg 13 | UV/40° | 20 hrs | AIBN | 1 mole % | benzene | 87 | $0.82^e$ | not soluble |
| | c | 230 mg 13 | UV/40° | 20 hrs | AIBN | 3 mole % | benzene | 95 | $0.52^e$ | not soluble |
| | c | 230 mg 13 | UV/40° | 20 hrs | AIGN | 3 mole % | $(CF_3)_2CHOH$ | 68 | | soluble, partially decomposed |

[a] 4-acryloxymethyl-2,6,7-trioxabicyclo[2.2.2]octane
[b] -methacryloxymethyl-2,6,7-trioxabicyclo[2.2.2]octane
[c] -methyl-4-methacryloxymethyl-2,6,7-trioxiabicyclo[2.2.2]octane
[d] Inherent viscosity measured in Ostwald viscosimeter in sulfolane at 30° C.
[e] Inherent viscosity measured in hexafluoroisopropanol at 30° C.

EXAMPLES 31-36

These examples illustrate the copolymerization of 4-acryloxymethyl-2,6,7-trioxabicyclo[2.2.2]octane with a variety of vinyl comonomers.

Benzene is dried over sodium and distilled just before use. Acetone was refluxed over potassium permanganate, distilled and redistilled over calcium hydride. Hexafluoroiospropanol was distilled from calcium hydride. Monomer, eventual comonomer, initiator and solvent are mixed in an ampoule, cooled to −78°, degassed, thawed, cooled and degassed again. Then the ampoule is sealed. At the end of the polymerization, attempts are made to dissolve the polymer and the whole is precipitated in hexane. The polymer is filtered off, dried and weighed.

Additional conditions, and the results, of each copolymerization are set forth in Table III as follows:

TABLE III
POLYMERIZATION OF 4-ACRYLOXYMETHYL-2,6,7-TRIOXABICYCLO[2.2.2]OCTANE

| Amount Orthoester Monomer | Vinyl Comonomer | Amount Co-monomer | Mole ratio Monomer-Co-monomer | Yield | Mole Ratio in Polymer |
|---|---|---|---|---|---|
| 200 mg | methyl acrylate | 43 mg | 66/33 | 120 mg/49% | 45/55 |
| 200 mg | methyl acrylate | 86 mg | 50/50 | 275 mg/96% | 40/60 |
| 200 mg | methyl methacrylate | 50 mg | 66/33 | 221 mg/88% | 56/44 |
| 200 mg | methyl methacrylate | 100 mg | 50/50 | 252 mg/84% | 41/59 |
| 200 mg | p-methoxystyrene | 67 mg | 66/33 | 113 mg/45% | 50/50 |
| 200 mg | p-methoxystyrene | 135 mg | 50/50 | 149 mg/49% | 40/60 |

Polymerization catalyst: 1 mole % azobisisobutyronitrile (AIBN)
Polymerization conditions: Ultraviolet (UV) light at 40° for 16 hours

EXAMPLE 37

This example illustrates the use of an ester herein, namely, 4-acryloxymethyl-2,6,7-trioxabicyclo[2.2.2]octane, in the preparation of a vinyl-acrylic copolymer textile crosslinking latex.

The following formulation was prepared:

| Component | Quantity |
|---|---|
| Vinyl Acetate | 360 g |
| Butyl Acrylate | 6.4 g |
| Acrylic Acid | 0.5 g |
| Acrylamide | 0.3 g |
| Duponol (Du Pont lauryl sulfate surfactant) | 3.0 g |
| Sodium Persulfate | 100 mg |
| Sodium Thiosulfate | 100 mg |
| Ferrous Sulfate | 0.5 mg |
| Water | 52 ml |
| 4-Acryloxymethyl-2,6,7-Trioxabicyclo[2.2.2] Octane | 400 mg |

Into a flask under nitrogen atmosphere are mixed half the amounts of indicated vinyl acetate, butyl acrylate, acrylic acid acrylamide and 4-acryloxymethyl-2,6,7-trioxabicyclo[2.2.2]octane, and the water and lauryl sulfate surfactant. The mixture is heated to 30° C. Half the indicated amount of sodium persulfate and sodium thiosulfate are added together with the ferrous sulfate. The temperature rises to 39° C. After cooling to 30° C., the remainder of all the reagents are added. The temperature rises to 37° C. Under continuous stirring, the reaction mixture, a polymer emulsion, is heated to 65° C. for 1 additional hour and thereafter the emulsion is brought to a pH of about 6 with ammonium hydroxide.

By way of evaluating the emulsion, two films were cast therefrom. The films (2 mil) on glass were hazy and when dry could not be lifted intact from the plate. The first film dried 48 hours at room temperature was attacked by acetone and while not completely dissolved, was softened and could easily be rubbed from the plate. Baking of the second film (air dried 24 hours) in an oven at 80° C. for 24 hours resulted in a visually unchanged sample which was observed to be resistant to acetone. While the film obviously absorbed acetone (blushed) it was not softened or weakened and was resistant to abrasion, even while soaking in the solvent. This evaluation demonstrates the utility of the foregoing emulsion as a latent cross-linking site for latex films.

What is claimed is:

1. An alpha, beta-ethylenically unsaturated orthoester of the general formula $$CH_2=\underset{\underset{R_1}{|}}{C}-\underset{\underset{\parallel}{O}}{C}-OCH_2-C\begin{pmatrix}CH_2-O\\CH_2-O\\CH_2-O\end{pmatrix}C-R_2$$

in which $R_1$ is hydrogen or a methyl group and $R_2$ is hydrogen or a lower alkyl group.

2. The alpha, beta-ethylenically unsaturated orthoester of claim 1 wherein $R_1$ is hydrogen and $R_2$ is hydrogen.

3. The alpha, beta-ethylenically unsaturated orthoester of claim 1 wherein $R_1$ is a methyl group and $R_2$ is hydrogen.

* * * * *